(12) United States Patent
Mori et al.

(10) Patent No.: US 10,984,527 B2
(45) Date of Patent: Apr. 20, 2021

(54) INTELLIGENT ATLAS FOR AUTOMATIC IMAGE ANALYSIS OF MAGNETIC RESONANCE IMAGING

(71) Applicant: THE JOHNS HOPKINS UNIVERSITY, Baltimore, MD (US)

(72) Inventors: Susumu Mori, Ellicott City, MD (US); Michael I. Miller, Towson, MD (US); Kenichi Oishi, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1283 days.

(21) Appl. No.: 15/221,865

(22) Filed: Jul. 28, 2016

(65) Prior Publication Data
US 2016/0335768 A1 Nov. 17, 2016

Related U.S. Application Data

(63) Continuation of application No. 13/695,173, filed as application No. PCT/US2011/034613 on Apr. 29, 2011, now abandoned.
(Continued)

(51) Int. Cl.
*G06T 7/00* (2017.01)
*A61B 5/055* (2006.01)
(Continued)

(52) U.S. Cl.
CPC .............. *G06T 7/0012* (2013.01); *A61B 5/00* (2013.01); *A61B 5/055* (2013.01); *A61B 5/72* (2013.01);
(Continued)

(58) Field of Classification Search
CPC .............. A61F 2/2875; A61F 2002/482; A61F 2002/3068; A61F 2/30942;
(Continued)

(56) References Cited

U.S. PATENT DOCUMENTS

| 6,226,418 B1 | 5/2001 | Miller et al. |
| 2003/0139659 A1* | 7/2003 | Dale .................... A61B 5/055 600/407 |

(Continued)

FOREIGN PATENT DOCUMENTS

| CN | 102646268 | * 8/2012 | ............... G06T 5/00 |

OTHER PUBLICATIONS

Miller, M., et al., "Mathematical textbook of deformable neuroanatomies", Proc. Natl. Acad. Sci. USA, (1993) vol. 90, pp. 11944-11948.
(Continued)

*Primary Examiner* — Amanda Lauritzen Moher
(74) *Attorney, Agent, or Firm* — MH2 Technology Law Group LLP

(57) ABSTRACT

A non-invasive imaging system, including an imaging scanner suitable to generate an imaging signal from a tissue region of a subject under observation, the tissue region having at least one substructure; a signal processing system in communication with the imaging scanner to receive the imaging signal from the imaging scanner; and a data storage unit in communication with the signal processing system, wherein the data storage unit stores an anatomical atlas comprising data encoding spatial information of the at least one substructure in the tissue region, and a pathological atlas corresponding to an abnormality of the tissue region, wherein the signal processing system is adapted to automatically identify, using the imaging signal, the anatomical atlas, and the pathological atlas, a presence of the abnormality or a pre-cursor abnormality in the subject under observation.

5 Claims, 9 Drawing Sheets

Related U.S. Application Data

(60) Provisional application No. 61/329,857, filed on Apr. 30, 2010.

(51) Int. Cl.

| | | |
|---|---|---|
| *A61B 6/03* | (2006.01) | |
| *A61B 6/00* | (2006.01) | |
| *A61B 5/00* | (2006.01) | |
| *G06T 7/143* | (2017.01) | |
| *G06T 7/174* | (2017.01) | |
| *G06T 7/246* | (2017.01) | |
| *G06T 7/149* | (2017.01) | |
| *G06K 9/62* | (2006.01) | |
| *G01R 33/563* | (2006.01) | |
| *G06K 9/42* | (2006.01) | |
| *G06T 15/00* | (2011.01) | |
| *G01R 33/20* | (2006.01) | |
| *G01R 33/56* | (2006.01) | |
| *G16H 50/20* | (2018.01) | |
| *G16H 50/50* | (2018.01) | |
| *G16H 50/30* | (2018.01) | |
| *G01T 1/29* | (2006.01) | |
| *G01T 1/161* | (2006.01) | |

(52) U.S. Cl.
CPC ............. *A61B 6/032* (2013.01); *A61B 6/037* (2013.01); *A61B 6/461* (2013.01); *A61B 6/50* (2013.01); *A61B 6/501* (2013.01); *A61B 6/52* (2013.01); *A61B 6/5217* (2013.01); *G01R 33/20* (2013.01); *G01R 33/5608* (2013.01); *G01R 33/56341* (2013.01); *G06K 9/42* (2013.01); *G06K 9/621* (2013.01); *G06K 9/6209* (2013.01); *G06K 9/6221* (2013.01); *G06K 9/6234* (2013.01); *G06T 7/0014* (2013.01); *G06T 7/143* (2017.01); *G06T 7/149* (2017.01); *G06T 7/174* (2017.01); *G06T 7/248* (2017.01); *G06T 15/00* (2013.01); *G16H 50/20* (2018.01); *G16H 50/30* (2018.01); *G16H 50/50* (2018.01); *A61B 5/004* (2013.01); *A61B 5/4064* (2013.01); *A61B 2576/00* (2013.01); *A61B 2576/02* (2013.01); *A61B 2576/026* (2013.01); *G01T 1/161* (2013.01); *G01T 1/2985* (2013.01); *G06K 2009/6213* (2013.01); *G06T 2207/10081* (2013.01); *G06T 2207/10088* (2013.01); *G06T 2207/10092* (2013.01); *G06T 2207/10104* (2013.01); *G06T 2207/10108* (2013.01); *G06T 2207/20221* (2013.01)

(58) Field of Classification Search
CPC ... A61F 2002/3067; A61F 2002/30948; A61B 5/0006; A61B 5/4836; A61B 5/0476; A61B 5/031; A61B 5/0066; A61B 5/0013; A61B 5/6868; A61B 5/686; A61B 5/4839; A61B 5/0084; A61B 5/055; A61B 5/743; A61N 1/3605; A61N 1/0531; A61N 1/00; G06T 2207/20128; G06T 7/00; G06T 7/0012; G06T 7/0014; G06T 7/0016; G06T 7/0081; G06T 7/73; G06T 7/75; A61M 5/14276; A61M 2210/0687; A61L 2430/02; G06K 9/2054; G06K 9/00; G06K 9/36; G06K 9/46; G06K 9/468; G06K 9/469; G06K 9/3233
See application file for complete search history.

(56) References Cited

U.S. PATENT DOCUMENTS

| | | | |
|---|---|---|---|
| 2004/0161138 A1* | 8/2004 | Ashton | G06T 7/11 382/128 |
| 2005/0273007 A1 | 12/2005 | Burbar et al. | |
| 2006/0142983 A1 | 6/2006 | Sorensen et al. | |
| 2007/0081706 A1 | 4/2007 | Zhou et al. | |
| 2007/0081707 A1 | 4/2007 | Sirohey et al. | |
| 2008/0144939 A1* | 6/2008 | Russakoff | G06K 9/6209 382/190 |
| 2008/0292194 A1* | 11/2008 | Schmidt | G06T 7/11 382/217 |
| 2010/0260396 A1* | 10/2010 | Brandt | G06K 9/4671 382/131 |
| 2013/0044927 A1* | 2/2013 | Poole | G06T 7/0014 382/131 |

OTHER PUBLICATIONS

Martin-Fernandez, M., et al., "Sequential anisotropic multichannel wiener filtering with rician bias correction applied to 3D regularization of DWI data", Medical Image Analysis (2009) vol. 13 pp. 19-35.

Lee, S., "Anisotropic Magnetic Colloids: a strategy to form complex structures using nonspherical building blocks", small (2009) vol. 5, No. 17, pp. 1957-1962.

Ding, Z., "Reduction of noise in diffusion tensor images using anisotropic smoothing", Magnetic Resonance in Medicine (2005) vol. 53, pp. 485-490.

Chen, B., "Noise removal in magnetic resonance diffusion tensor imaging", Magnetic Resonance in Medicine (2005) vol. 54, pp. 393-407.

Hecke, W., "Comparing isotropic and anisotropic smoothing for voxel-based DTI analyses: a simulation study", Human Brain Mapping (2010) vol. 31, pp. 98-114.

Xu, Q., "Efficient anisotropic filtering of diffusion tensor images", Magnetic Resonance Image (2010) vol. 28, pp. 200-211.

Mori, S., "Stereotaxic white matter atlas based on diffusion tensor imaging in an ICBM template", Neuroimage, Apr. 1, 2008, vol. 40, No. 2, pp. 570-582.

Oishi, K., et al., "Human brain white matter atlas: identification and assignment of common anatomical structures in superficial white matter", Neuroimage, Nov. 15, 2008, vol. 43, No. 3, pp. 447-457.

Oishi, K., et al., "Atlas-based whole brain white matter analysis using large deformation diffeomorphic metric mapping: application to normal elderly and alzheimer's disease participants", Neuroimage, Jun. 2009, vol. 46, No. 2, pp. 486-499.

Smith, S., et al., "Tract-based spatial statistics: voxelwise analysis of multi-subject diffusion data", NeuroImage (2006) vol. 31, pp. 1487-1505.

Grenander, U., et al., "Computational Anatomy: an emerging discipline", Statistical Computing & Graphics, (1996) vol. 7, No. 3.

Joshi, S., et al., "Hierarchical brain mapping via a generalized dirichlet solution for mapping brain manifolds", In Proceedings of Spie—The International Society for Optical Engineering, Aug. 1995.

Zou K., et al., (2007) "Receiver-operating characteristic analysis for evaluating diagnostic tests and predictive models", Circulation, vol. 115, pp. 654-6578.

* cited by examiner

INTELLIGENT ATLAS FOR AUTOMATIC IMAGE ANALYSIS OF MAGNETIC RESONANCE IMAGING

CROSS-REFERENCE OF RELATED APPLICATION

This application is a Continuation of U.S. patent application Ser. No. 13/695,173, filed Mar. 8, 2013, which is a 35 U.S.C. § 371 U.S. national entry of International Application PCT/US2011/034613, having an international filing date of Apr. 29, 2011, which claims the benefit of U.S. Provisional Application 61/329,857, filed Apr. 30, 2010, the content of each of the aforementioned applications is herein incorporated by reference in their entirety.

STATEMENT OF GOVERNMENTAL SUPPORT

This invention was made with government support under grant numbers R01AG020012 and P41RR015241, awarded by the National Institutes of Health. The government has certain rights in the invention.

BACKGROUND

Field of Invention

The current invention relates to non-invasive imaging systems and methods, and more particularly to imaging systems and methods that provide computer assisted diagnosis of tissue abnormalities in human and animal subjects.

Discussion of Related Art

Conventional radiological diagnosis can be qualitative or subjective. Even though quantitative analyses may significantly improve our ability to detect and characterize abnormalities, currently almost no quantitative techniques can be accepted as a part of routine radiological diagnosis. This is partly due to difficulties in analyzing tissue based on radiological, such as Magnetic Resonance (MR) images. For example, high quality segmentation of the brain boundary requires a considerable amount of manual labor, which typically takes 2-4 hours for individual brains. Further segmentation of the brain into tissue substructures takes even more time. There are many automated programs for various types of tissue segmentation but they can only provide approximate results. For automated image analysis, voxel-based analyses (VBAs) have been widely used. Initially, the shape of each brain may be transformed to that of an atlas brain. Once all brain images are transformed (normalized) to the atlas, voxel-by-voxel analyses can be performed. In this type of analysis, each voxel is treated as an independent entity and no anatomical information is used during the process. This approach has not proven to be effective and there is a need in the art for an automatic means to improve the ability to detect and characterize abnormalities from current radiological images.

SUMMARY

An embodiment of the present invention includes a non-invasive imaging system, including an imaging scanner suitable to generate an imaging signal from a tissue region of a subject under observation, the tissue region having at least one substructure; a signal processing system in communication with the imaging scanner to receive the imaging signal from the imaging scanner; and a data storage unit in communication with the signal processing system, wherein the data storage unit stores an anatomical atlas comprising data encoding spatial information of the at least one substructure in the tissue region, and a pathological atlas corresponding to an abnormality of the tissue region, wherein the signal processing system is adapted to automatically identify, using the imaging signal, the anatomical atlas, and the pathological atlas, a presence of the abnormality or a pre-cursor abnormality in the subject under observation.

Some embodiments of the present invention include a workstation, including a receiving engine adapted to receive an image data representing a tissue region of a subject, an anatomical atlas comprising data encoding spatial information of at least one anatomical substructure in the tissue region, and a pathological atlas comprising data encoding spatial information of a portion of the at least one anatomical substructure affected by an abnormality of the tissue region and statistical quantities associated with the portion of the at least one substructure; a normalizing engine constructed to provide a normalized image data by normalizing the image data, via a transformation, to the anatomical atlas; a computing engine configured compute a statistical quantity from image voxels in the normalized image data corresponding to the portion of the at least one anatomical substructure affected by an abnormality of the tissue region; and an analyzing engine configured to determine whether the abnormality or a pre-cursor abnormality thereof is present in the subject by analyzing a statistical relationship between the statistical quantity computed from the image data and the statistical quantities in the pathological atlas.

Some embodiments of the present invention include a method of generating a pathological atlas corresponding to an abnormality, including: receiving, from one of an imaging system, a workstation, or a first data storage device, a first image data representing a tissue region having a plurality of anatomical substructures; wherein the first image data comprises a plurality of image voxels, and wherein the abnormality affects at least one of the plurality of anatomical substructures, providing a normalized first image data by normalizing the first image data, via a transformation, to an anatomical atlas corresponding to the tissue region; wherein the anatomical atlas comprises data encoding spatial information of the plurality of anatomical substructures, and wherein the anatomical atlas is from one of the first data storage device, or a second data storage device; creating the pathological atlas corresponding to the abnormality based on the normalized first image data; wherein the pathological atlas comprises data encoding spatial information of the at least one of the plurality of anatomical substructures affected by the abnormality; and storing the pathological atlas corresponding to the tissue abnormality on the data storage system.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing the embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
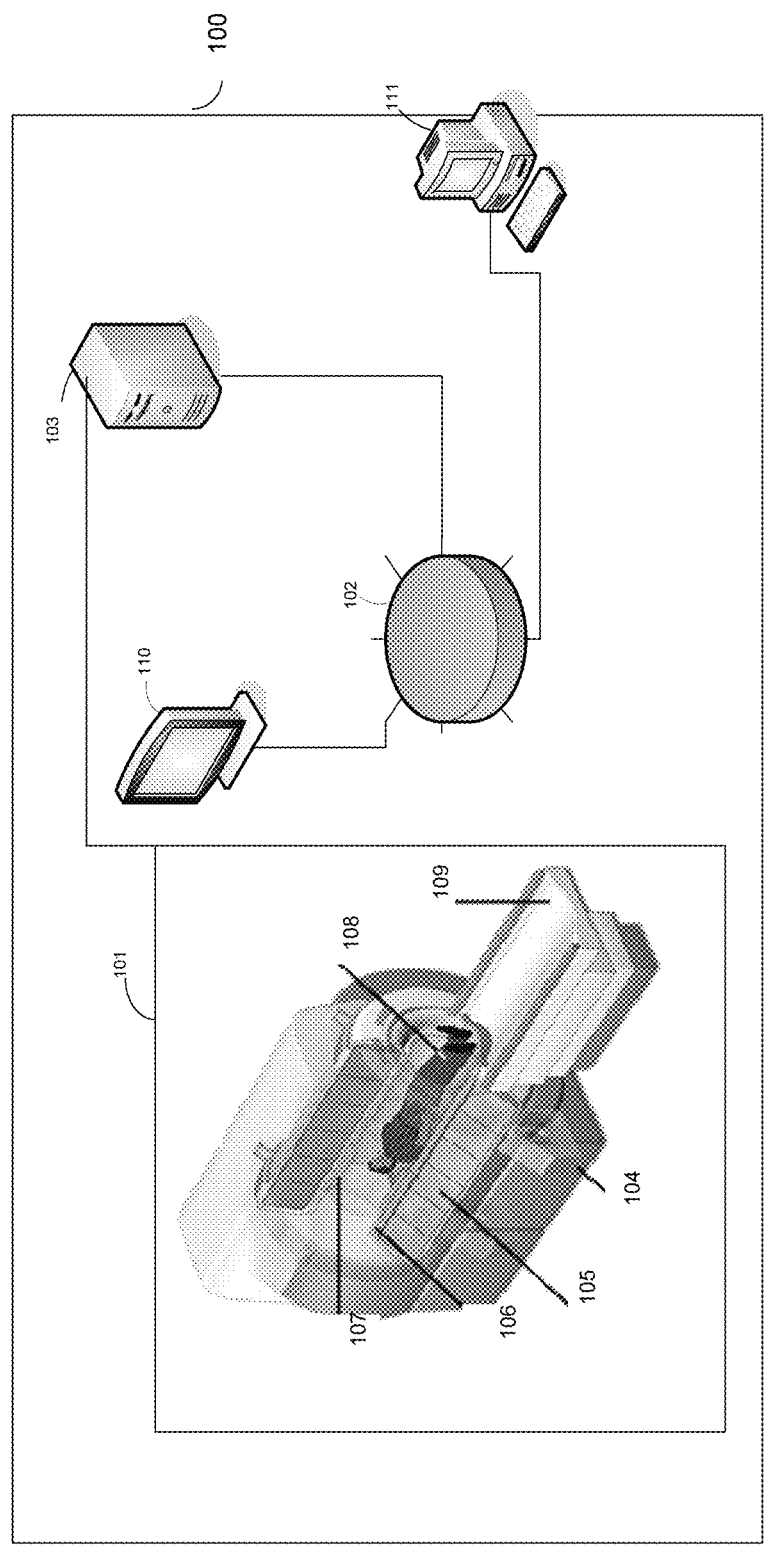
FIG. 1 is a schematic illustration of a non-invasive imaging system according to an embodiment of the current invention.

FIG. 1 is a schematic illustration of a non-invasive imaging system 100 according to some embodiments of the current invention. The non-invasive imaging system 100 includes an imaging scanner 101, a data storage unit 102, and a signal processing system 103. Imaging scanner 101 may be, but is not limited to, a magnetic resonance imaging (MRI) scanner, a computed tomography (CT) scanner, a positron emission tomography (PET) scanner, a single positron emission computed tomography (SPECT) scanner, or combinations thereof. For example, an MRI scanner may have a base 104 to support a main magnet 105 (providing a substantially uniform main magnetic field $B_0$ for a subject 108 under observation on scanner bed 109), a gradient system 106 (providing a perturbation of the main magnetic field $B_0$ to encode spatial information of the constituent water molecules of subject 108 under observation), and a radio-frequency (RF) coil system 107 (transmitting electromagnetic waves and receiving magnetic resonance signals from subject 108).

Data storage unit 102 stores atlas data corresponding to a tissue region of subject 108 under observation. The tissue region may be, for example, a brain, a heart, a liver, a muscle, and other intended organ of subject 108. The term "atlas" used herein does not necessarily require an actual material object, such as a three dimensional material object. It will be used generally to also refer to data or information that represents a geometrical configuration.

For example, data storage unit 102 may store an anatomical atlas of the tissue region including geometric information of the constituent anatomical substructures. For example, the anatomical atlas may represent a human brain and may include information encoding locations of the gray matter, the white matter, etc. The anatomical atlas may be derived from, for example, a plurality of images from a subpopulation of subjects similar to subject 108. For example, the images can come from the same age group as subject 108 in some applications. This is because each age range may have different tissue shapes and contrasts. The anatomical atlas can be constructed to take into account variations between genders, races, or other subpopulations based on the potential application.

Data storage unit 102 may further store a pathological atlas including, for example, geometric information of substructures affected by, for example, a brain pathology (such as, for example, Alzheimer's disease, mild-cognitive disability, Parkinson's disease, dementia, etc.), a liver disease, a kidney disease, a muscle abnormality (e.g., atrophy, edema, or frailty, etc.), a joint abnormality, etc. The pathological atlas may also be referred to as the disease specific atlas (DSA). The pathological atlas may be derived from, for example, a plurality of images from a subpopulation of patients having, for example, the specific brain pathology or precursor disease to the specific brain pathology (e.g., mild cognitive impairment-converter as a precursor to Alzheimer's disease).

The plurality of images, used to construct the anatomical and pathological atlas, may be, for example, MRI images, CT images, PET images, SPECT images, etc. the anatomical and pathological atlas may incorporate information from images from at least one subject that is different from subject 108 under observation. The anatomical and pathological atlas may incorporate information from images from a previous scan of subject 108 under observation. The anatomical and pathological atlas may be derived from images of a variety of different contrasts, each favorably delineating, for example, certain substructures in the tissue region. For example, $T_1$-weighted magnetic resonance images suitable for the cortex and deep gray matter structures of the brain may be used. For example, $T_2$-weighted magnetic resonance images having higher contrasts for the ventricles of the brain may be used. For example, diffusion tensor images in which intra-white matter structures of the brain are best delineated may be used.

The anatomical atlas may include spatial information, such as, for example, shape information, location information, of the tissue region. The anatomical and pathological atlas may further incorporate variability information associated with registering the soft tissue region in the images from a subpopulation of subjects to the geometric information. Registering a soft tissue region in an image from a subject to the geometric information of a atlas may involve warping or transforming (e.g., translation, scaling, deforming, etc.) the soft tissue region in the image to align with the geometric information of the atlas. Registering may also be referred to as normalizing.

The pathological atlas may include spatial information, such as, for example, shape information, location information, transformation information when registering an image from subject 108 to the anatomical atlas, of a portion of the anatomical substructures the tissue region affected by an abnormality (such as, for example, a brain pathology). The pathological atlas may further comprise statistical information associated with the portion of the anatomical substructures affected by the abnormality. The statistical information may be computed from image voxels corresponding to the portion of the anatomical substructures affected by the abnormality in the tissue region.

The term "atlas" include, but is not limited to the above examples.

Data storage unit 102 may be, for example, a hard disk drive, a network area storage (NAS) device, a redundant array of independent disks (RAID), a flash drive, an optical disk, a magnetic tape, a magneto-optical disk, etc. However, the data storage unit 102 is not limited to these particular examples. It can include other existing or future developed data storage devices without departing from the scope of the current invention.

Signal processing system 103 is in communication with imaging scanner 101 to receive imaging signals for forming images of subject 108. Signal processing system 103 may be partially or totally incorporated within a structure housing imaging scanner 101. Signal processing system 103 may be at least partially incorporated in a workstation that is structurally separate from and in communication with imaging scanner 101. Signal processing system 103 may be incorporated in a workstation that is structurally separate from and in communication with imaging scanner 101. Imaging signals received by signal processing system 103 may be associated with, for example, a magnetic resonance contrast parameter, such as, for example, a relaxation time $T_1$, a relaxation time $T_2$, an apparent diffusion coefficient, a property associated with the blood oxygenation level dependent (BOLD) effect, a property associated with the diffusion tensor, etc.

Signal processing system 103 is in communication with data storage unit 102. Signal processing system 103 is adapted to automatically identify, using said imaging signal, said anatomical atlas, and said pathological atlas, a presence of the abnormality of the tissue region in the subject 108 under observation. The imaging signals being processed by signal processing system 103 may contain multiple contrasts mechanisms, each favorably delineating a portion of the substructures of the tissue region. At least one contrast mechanism is taken into account when the signal processing system 103 automatically identifies the presence of the abnormality or a precursor of the abnormality. For example, imaging signals may be Diffusion Tensor Imaging (DTI) signals from a variety of information may be computed, such as, for example, fiber anisotropy, mean diffusivity, parallel diffusion ($\lambda|$), and radial diffusion ($\lambda\perp$). In addition, $T_2$ maps, $T_1$ maps may also be calculated from the imaging signals.

The diagnosis results may be visualized by superimposing the pathological atlas on the normalized image on a viewing station 110 or a console station 111. Viewing station 110 or a console station 111 may be, for example, a display device or a printing device. Example display devices may include, for example, a cathode ray tube (CRT), a light-emitting diode (LED) display, a liquid crystal display (LCD), a digital light projection (DLP) monitor, a vacuum florescent display (VFDs), a surface-conduction electron-emitter display (SED), a field emission display (FEDs), a liquid crystal on silicon (LCOS) display, etc. Example printing devices may include, for example, toner-based printers, liquid ink-jet printers, solid ink printers, dye-sublimation printers, and inkless printers such as thermal printers and ultraviolet (UV) printers, etc.

Figure 2A:
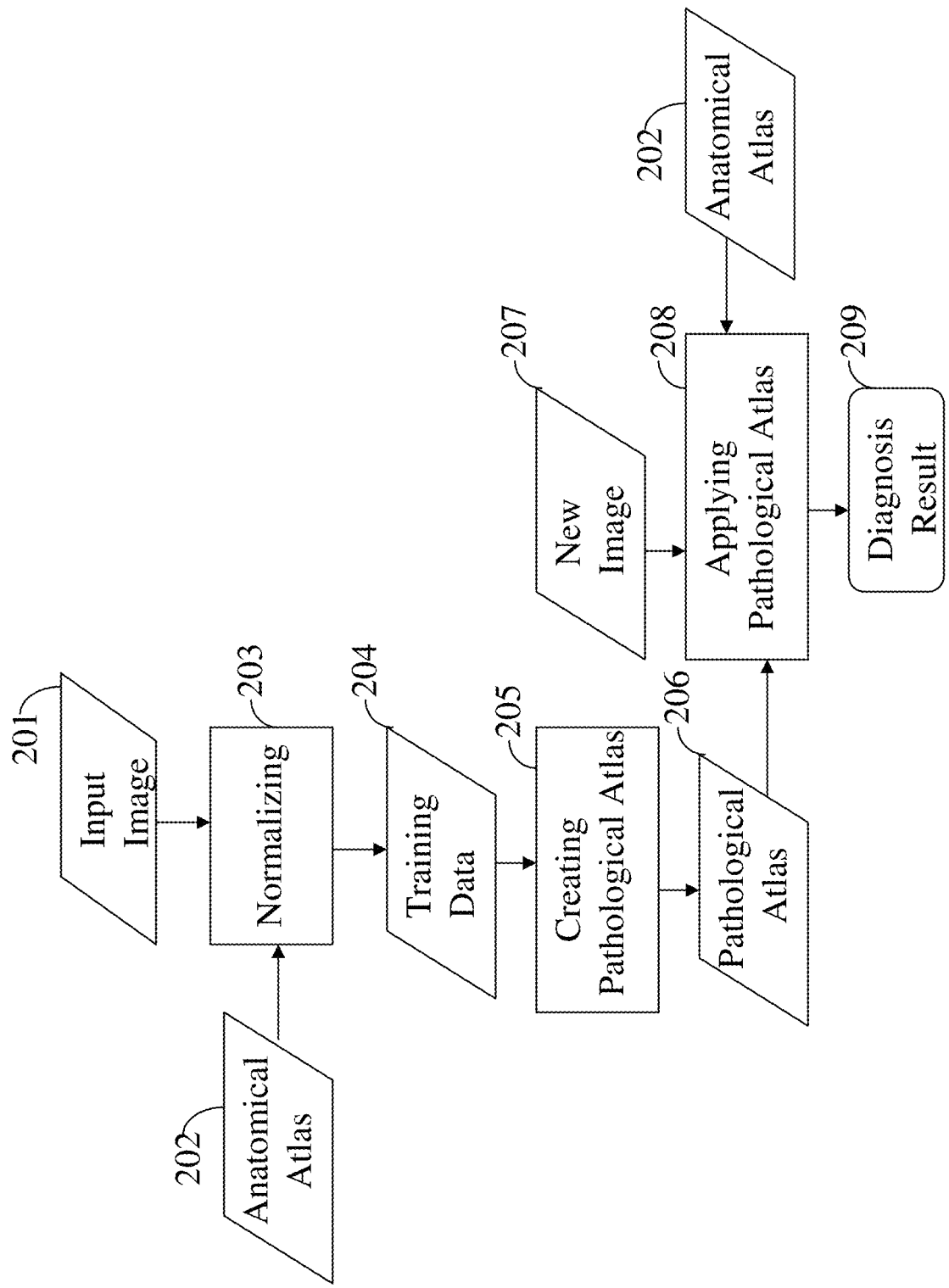
FIG. 2A shows a flow chart according to some embodiments of the current invention.

FIG. 2A shows a flow chart illustrating processes, implemented by one or more processors executing software code stored on one or more data storage devices, according to some embodiments of the current invention. The processors may be signal processors, computer processors, or combinations thereof. Example signal processors may include programmed field programmable gated array (FPGA) chips, programmed digital signal processing (DSP) chips, application specific integrated circuits (ASIC) chips, etc. Example computer processors may include single core or multi-core central processing units (CPU), single-core or multi-core graphic unit processing (GPU) chips, etc. In some embodiments of the current invention, the processes illustrated in FIG. 2A can be performed by data storage unit 102 and signal process unit 103.

Figure 2B:
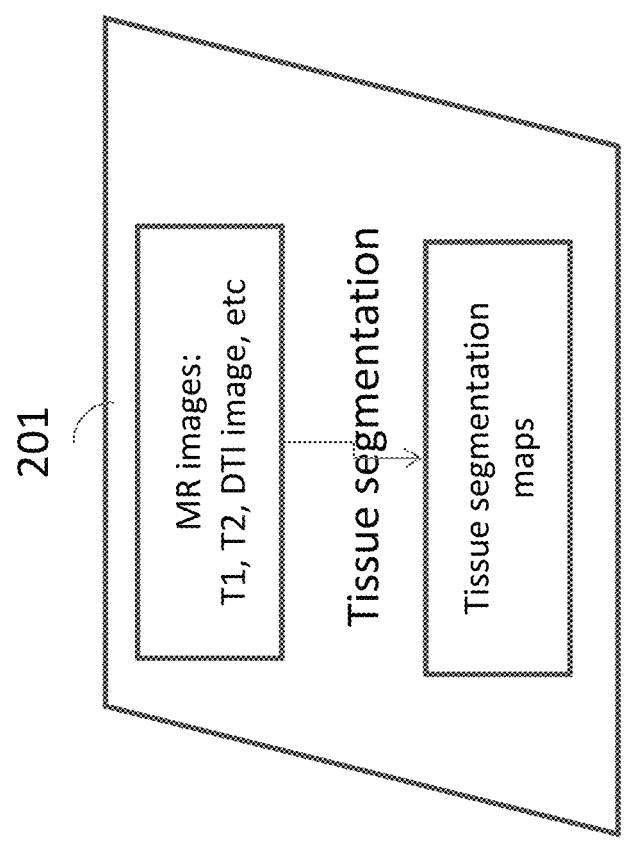
FIG. 2B shows an example input image 201 according to some embodiments of the current invention.

Block 201 corresponds to an input image, which can be an image from a single subject or a population-averaged image. Input image 201 corresponds to a tissue region having at least one substructure. Input image 201 may be more than one image showing the tissue region from at least one subject from at least one of an imaging system or a data storage device. FIG. 2B shows an example input image 201 according to some embodiments of the current invention. Input image 201 may include, for example, Diffusion Tensor Image (DTI) and $T_2$ image. Input image 201 may further include $T_1$ weighted images. Images may be processed to show segmented structures of the brain tissue. The processing may be manual or automatic.

Block 202 represents an anatomical atlas including spatial information of the tissue region, as discussed above.

In block 203, input image 201 is normalized to anatomical atlas 202. Registration may involve warping or transforming (e.g., translation, scaling, deforming, etc.) the soft tissue region in the images to align with the shape information of anatomic atlas 202. A transformation algorithm, called Large Deformation Diffeomorphic Metric Mapping (LDDMM) (Miller et al., 1993, Proc Natl Acad Sci, 90, 1194-11948; Joshi et al., 1995, Geometric methods in Applied Imaging, San Diego, Calif.; Granander and Miller, 1996, Statistical computing and graphics newsletter 7, 3-8), may be used during the registration. There can be several important technically attractive features of LDDMM. First, LDDMM is highly non-linear and can match the shapes of two brains. It can even transform a brain with severe atrophy. Second, LDDMM can achieve topology preservation. Topology preservation may be a very important feature when applying a morphing algorithm to a biological entity. For example, when morphing one face to another, if topology is not preserved, non-biological results can occur (e.g., two eyes become three eyes). Third the transformation can be reciprocal. Other transformation algorithms that can generate image transformation and preserve tissue topology can be used instead of LDDMM. In some cases, e.g. when only subtle changes in soft tissue regions are expected, the requirement of topology preserving can be waived.

Figure 2C:
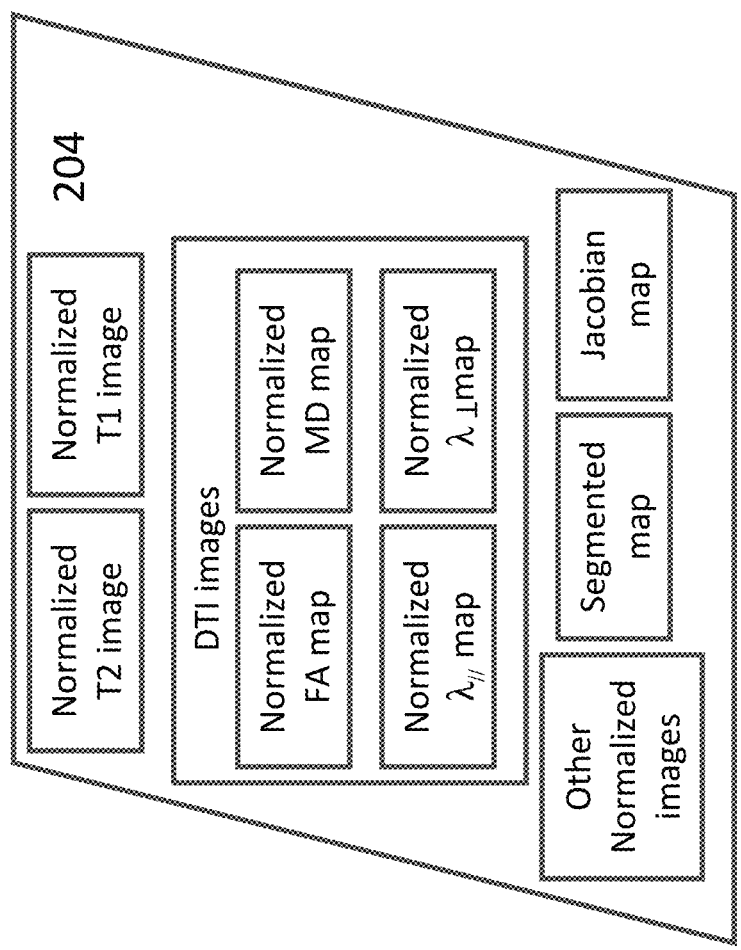
FIG. 2C shows an example training data 204 according to some embodiments of the present invention.

Training data 204 may be generated by normalizing block 203 and may be used to create pathological atlas 206 via block 205. FIG. 2C shows an example of training data 204 according to some embodiments of the present invention. Training data 204 may include a normalized $T_2$ image, a normalized $T_1$ image, Diffusion Tensor Image (DTI) images, other normalized images, a segmented structure map, and a Jacobian map. DTI map may include a normalized Fiber Anisotropy (FA) map, a normalized Mean Diffusivity (MD) map, a normalized parallel diffusion ($\lambda|$) map, a normalized radial diffusion ($\lambda\perp$) map. A Jacobian map shows the transformation matrix of the normalization process.

Figure 2D:
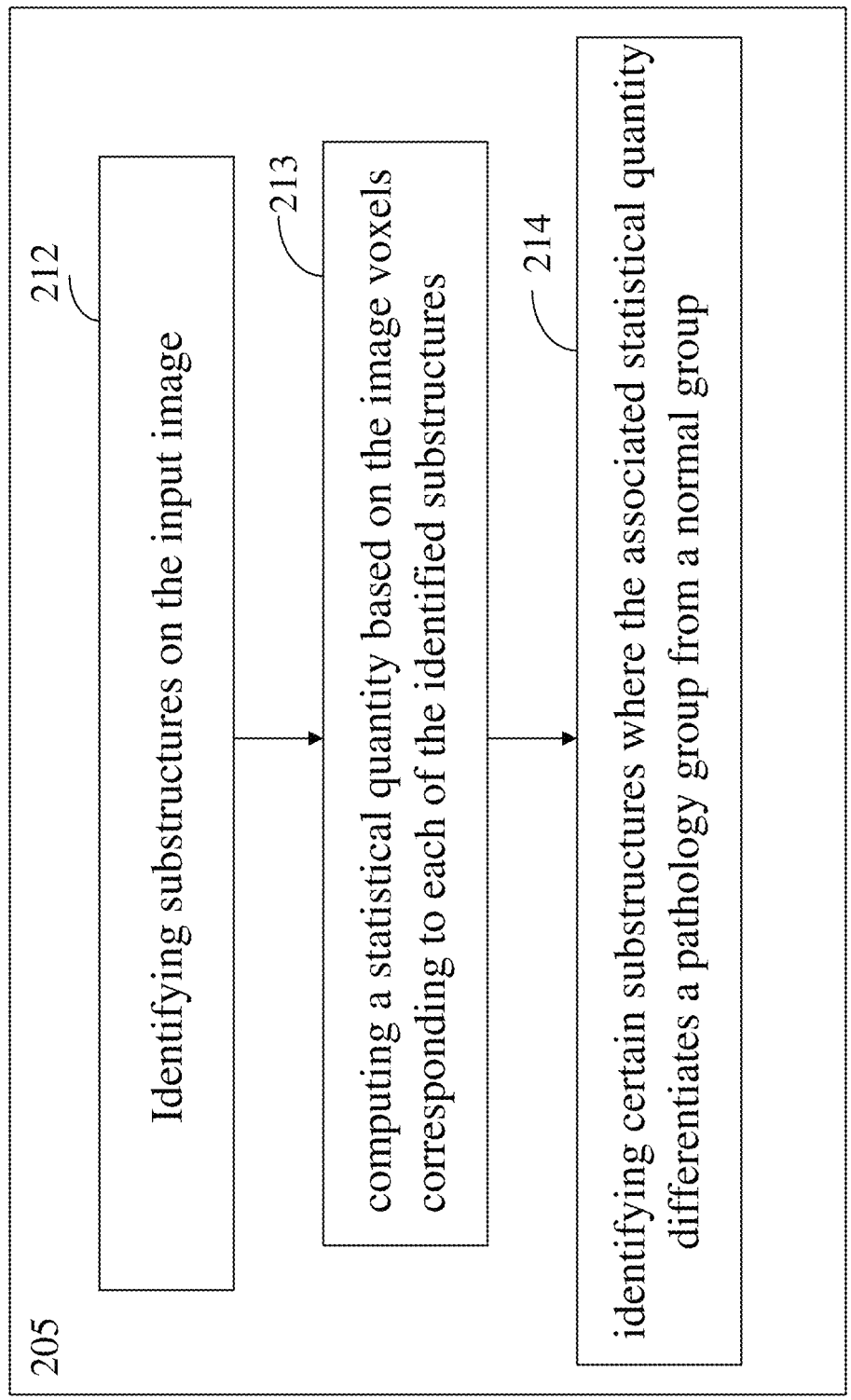
FIG. 2D shows one example implementation of block 205 according to an embodiment of the present invention.

FIG. 2D shows one implementation of block 205 according to an embodiment of the present invention. In block 212, the locations of at least some anatomical substructures of the tissue region may be identified in the input image. The structure could be as small as a single pixel or could be clusters of pixels. In block 213, a statistical quantity may be computed based on a portion of the image voxels corresponding to these anatomical substructures. These image pixels may be associated with the normalized input image 204. The statistical quantities of a subset of these anatomical structures may exhibit a statistically significant differentiation between a disease group having the abnormality (or a precursor condition) and a normal control group. Once the statistical significant difference is confirmed in block 214, the statistical quantities computed this subset of anatomical structures may be stored in the pathological atlas 206. In particular, the statistically significant differentiation may be determined via a Linear Discriminatory Analysis (LDA) to substantially improve a classification power of using said statistic quantity. The Linear Discriminatory Analysis (LDA) may include permutation tests and a Receiver Operating Characteristic (ROC) analysis, as will be demonstrated below.

Figure 2E:
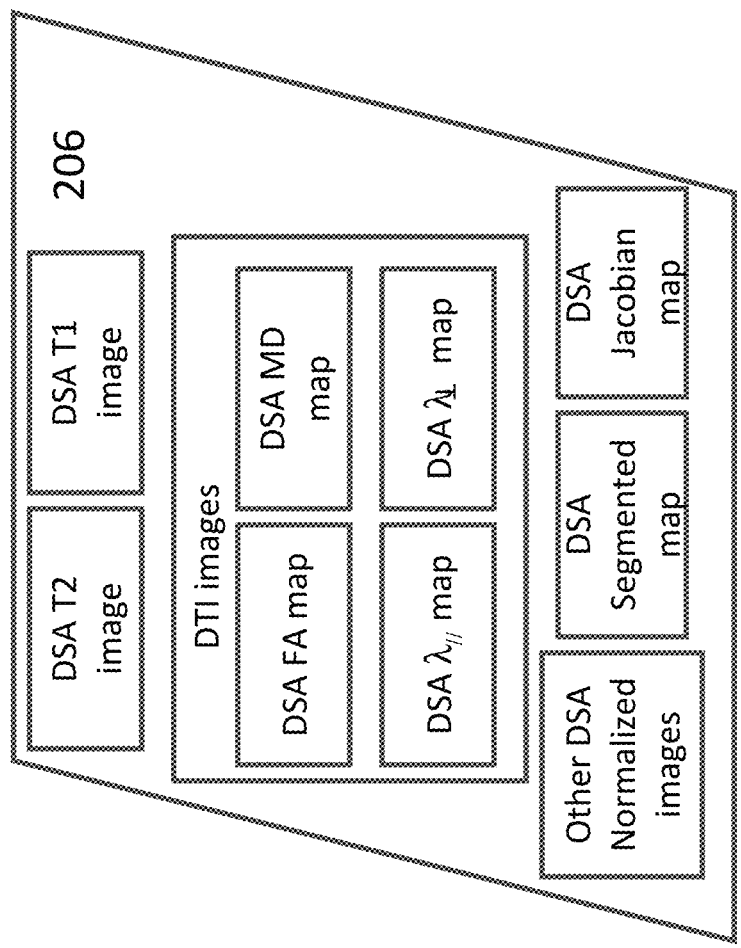
FIG. 2E shows an example pathological atlas 206 according to some embodiments of the present invention.

FIG. 2E shows an example pathological atlas 206 according to some embodiments of the present invention. Pathological atlas 206 may include Disease Specific Atlas (DSA) data including a DSA $T_2$ image, a DSA $T_1$ image, DSA DTI images. The DSA DTI images may include a DSA Fiber Anisotropy (FA) map, a DSA Mean Diffusivity (MD) map, a DSA parallel diffusion ($\lambda|$) map, a DSA radial diffusion ($\lambda\perp$) map. Pathlogical atlas 206 may further include a DSA segmented map, a DSA Jacobian map showing the characteristic transformation matrix of the normalization, or other DSA normalized images. Disease specific means specific and characteristic to a particular abnormality. The abnormality may include, for example, a brain disease including a neurodegenerative disease (such as, for example, Alzheimer disease, Parkinson's disease, Wilson's disease, mild-cognitive impairment, dementia, etc.), a liver disease, a kidney disease, a muscle abnormality (such as, for example, muscle atrophy, muscle edema, muscle frailty, etc,) or a joint abnormality (such as, for example. Rheumatoid arthritis, ostero-arthritis, etc.).

In block 208, anatomical atlas 202, pathological atlas 206 are applied to new image 207 from the tissue region of a new subject to automatically identify the presence of the abnormality in the new subject.

Figure 2F:
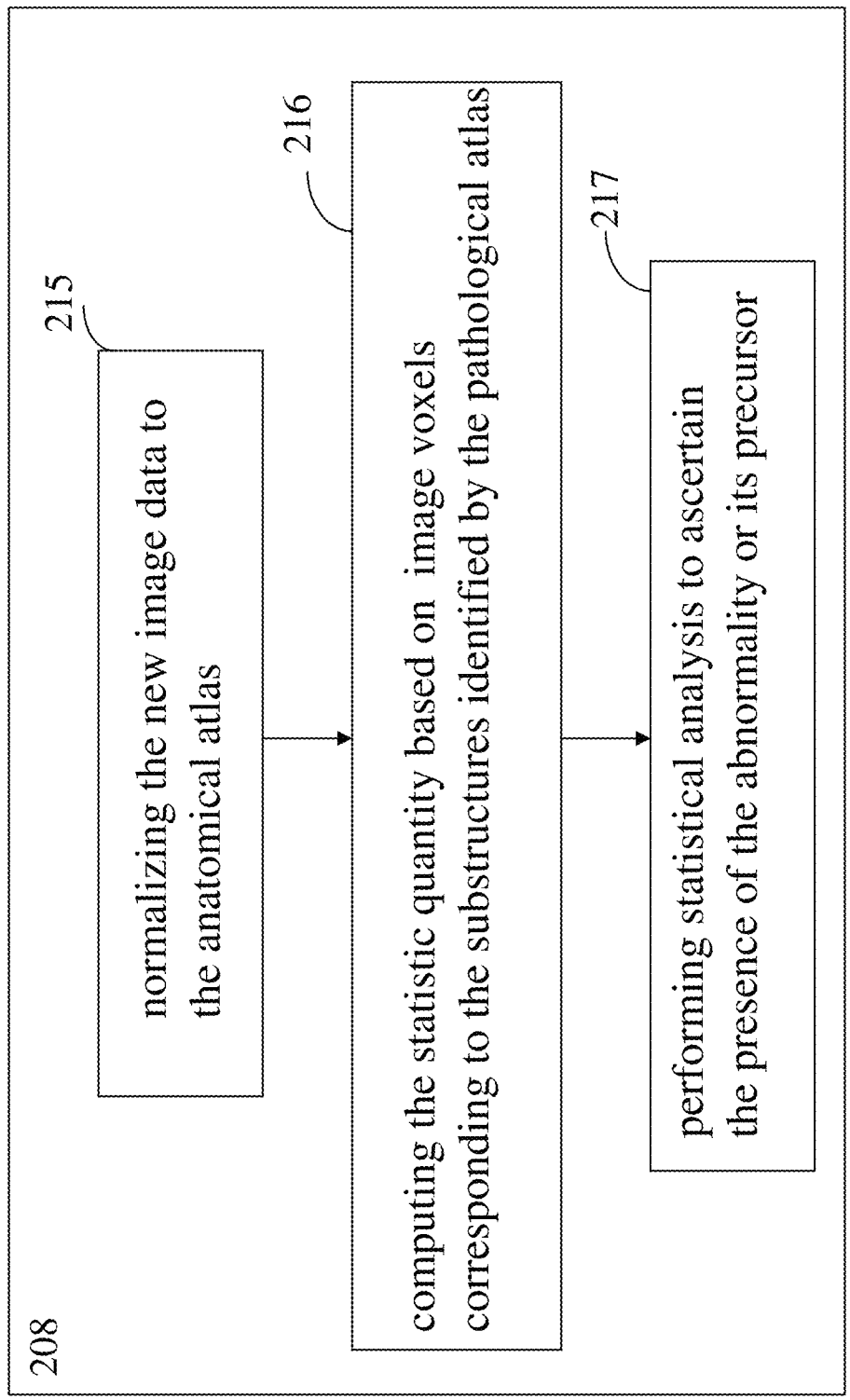
FIG. 2F shows an implementation of block 208 according to some embodiments of the present invention.

FIG. 2F shows an implementation of block 208 according to some embodiments of the present invention. In block 215, new image 207 is normalized to anatomical atlas 202 according to the same registration procedure as discussed above. In block 216, a statistical quantity (such as, for example, an average value, a median value, etc.) of image voxels corresponding to each of these anatomical substructures affected by the abnormality may be computed. In block 217, the computed statistical quantity for an affected anatomical structure may be analyzed to determine a statistical relationship with the statistical quantity stored in the pathological atlas 206. The analysis may automatically identify the presence of the abnormality in the new subject. The analysis can may be a form of a classification to determine the probability that the computed statistical quantity based on new image 207 is in the same class as the stored statistical quantities in the pathological atlas 206.

Thus, the atlas-based approach, as compared to a conventional voxel-based approach has been disclosed. In this type of analysis, the atlas may be pre-segmented into anatomical substructures based on anatomical knowledge. After normalization of an input image to an anatomical atlas, the tissue region can be automatically segmented into the defined anatomical substructures, which allows substructure-specific morphometry and photometry. All voxels within a substructure may be pooled for analyses. This can potentially enhance the statistical power and help anatomical interpretation of the voxel-based analyses, as demonstrated below.

Figure 3:
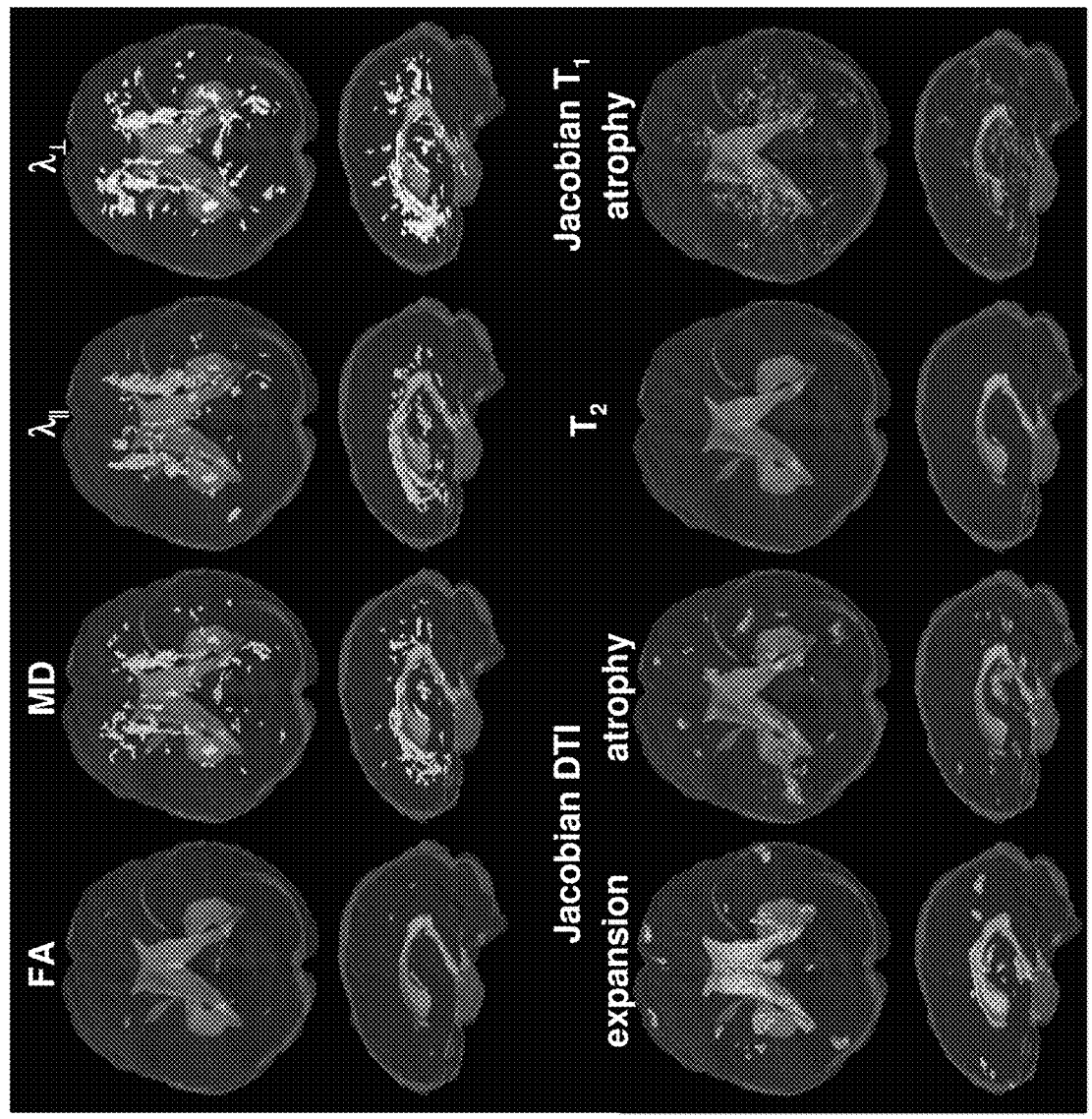
FIG. 3 shows an example of multi-contrast disease-specific atlas created for Alzheimer's disease.

FIG. 3 shows an example of disease-specific atlas of Alzheimer's disease. For each image contrast, sensitive brain areas are defined in the common anatomical space (atlas). This anatomical template can be applied to each patient and quantify the values of multiple contrasts. A linear combination of these contrast values, for example, can be used as an index to represent the likelihood of being the specific disease of interest.

Figure 4:
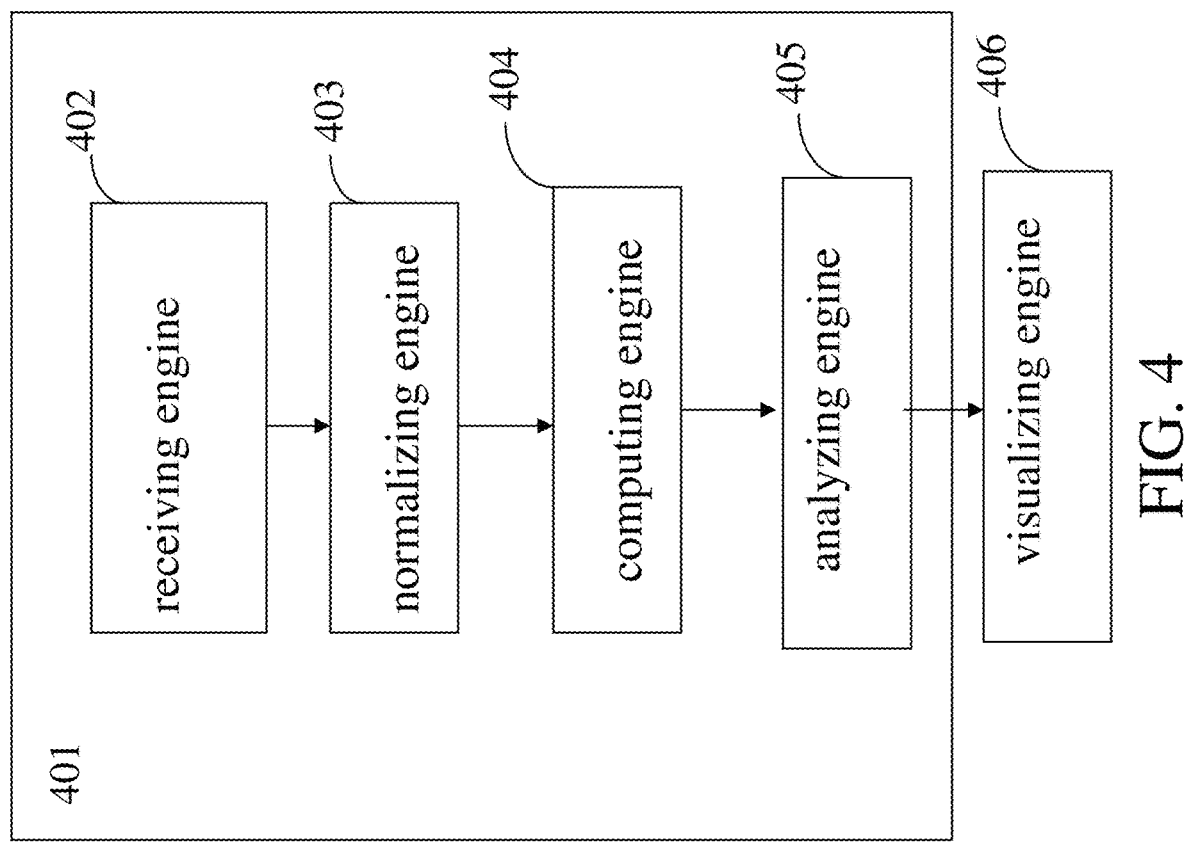
FIG. 4 shows a workstation according to some embodiments of the current invention.

FIG. 4 shows a workstation 401 according to some embodiments of the current invention. The workstation may include a receiving engine 402, a normalizing engine 403, a computing engine 404, and analyzing engine 405.

Receiving engine 402 may be adapted to receive an image data representing a tissue region of a subject, an anatomical atlas comprising data encoding spatial information of at least one anatomical substructure in the tissue region, and a pathological atlas comprising data encoding spatial information of a portion of the at least one anatomical substructure affected by an abnormality of the tissue region and statistical quantities associated with the portion of the at least one substructure. The received image data may have at least one contrast type that favorably delineates at least some of the substructure of the tissue region.

Normalizing engine 403 may be constructed to provide a normalized image data by normalizing the image data, via a transformation, to the anatomical atlas.

Computing engine 404 may be configured compute a statistical quantity from image voxels in the normalized image data corresponding to the portion of the at least one anatomical substructure affected by an abnormality of said tissue region.

Analyzing engine 405 may be configured to determine whether said abnormality or a pre-cursor abnormality thereof is present in said subject by analyzing a statistical relationship between the statistical quantity computed from said image data and the statistical quantities in the pathological atlas.

Workstation 401 may further include a visualization engine 406 to display the registered at least one image showing the tissue region. Visualization engine 406 may be, for example, a display device or a printing device. Example display devices may include, for example, a cathode ray tube (CRT), a light-emitting diode (LED) display, a liquid crystal display (LCD), a digital light projection (DLP) monitor, a vacuum florescent display (VFDs), a surface-conduction electron-emitter display (SED), a field emission display (FEDs), a liquid crystal on silicon (LCOS) display, etc. Example printing devices may include, for example, toner-based printers, liquid ink-jet printers, solid ink printers, dye-sublimation printers, and inkless printers such as thermal printers and ultraviolet (UV) printers, etc.

Workstation 401 may be a computer with at least one central processing unit (CPU) and a plurality of memories. Workstation 401 may also be a dedicated processing machine with such devices as, for example, a field programmable gated array (FPGA), a digital signal processing (DSP) chip, a graphic processing unit (GPU), an application specific integrated circuit (ASIC), etc. Workstation 401 may also be incorporated in the imaging system 100.

The engines may be implemented by a computer with at least one processor and a plurality of memories. The processor may be, for example, one or more single-core or multi-core central processing unit (CPU), one or more single-core or multi-core graphic processing unit (GPU), etc. The computer may be a distributed computer comprising more than one processor connected via a network to divide the computation. Example networks may include, but is not limited to, an intranet, an extranet, the interne, or combinations thereof. Receiving engine 402, normalization engine 403, computing engine 404, and analyzing engine 405 may be implemented by, for example, a field programmable gated array (FPGA), a digital signal processing (DSP) chip, a graphic processing unit (GPU), an application specific integrated circuit (ASIC), etc.

In general, normalization-based image analysis, in which voxel-by-voxel statistical analysis (VBA) is performed after the brain shapes are normalized to an atlas space, is widely used to detect differences in MR images between normal populations and patient populations. While this approach provides a method for an automated and quantitative examination of the entire brain with the highest spatial information, there exists several important limitations. First, perfect spatial normalization accuracy is not assured. Second, the information from each pixel is noisy. Due to these limitations, VBA often does not have enough power to differentiate the patient population from the normal population nor can it be used for diagnosis of individual patients. To increase the statistical power, it is common practice to apply spatial filtering that averages the information from multiple adjacent voxels. The most popular filtering method is an isotropic filter (typically 3-16 mm) that effectively lowers the spatial resolution and increases the partial volume effect. This counteracts one of the most important advantages of MRI; highly localized spatial information, which enables delineation of the fine detail of brain anatomy. To ameliorate this problem, structure-based (non-isotropic) spatial filtering methods have been postulated. These methods include anisotropic spatial filtering (Chen and Hsu, 2005; Ding et al., 2005; Lee et al., 2009; Martin-Fernandez et al., 2009; Van Hecke et al., 2010; Xu et al., 2010), skeletonization of the white matter structures (Smith et al., 2006), and parcellation of the brain structures (Mori et al., 2008; Oishi et al., 2009; Oishi et al., 2008). Although these sophisticated filtering methods could possibly increase the statistical power to separate patients from normal controls, it is difficult to choose a single spatial filtering method suitable for all diseases, because the volume and the spatial distribution of the abnormalities depend on the nature of the disease. For example, if the pathology of the disease follows a vascular pattern, cytoarchitecture-based filtering may not a logical choice. If the pathology is limited to a small area in the structure, parcellation-based filtering may be spatially too coarse to detect the abnormality. If the purpose of the analysis is to investigate known pathological features of a particular disease, a disease-specific filtering method could possibly increase the statistical power; namely, groups of voxels at specific locations are extracted and averaged for statistical analysis. To test this hypothesis, multi-contrast, disease-specific atlases were developed, specifying voxel locations in standard coordinates that represent the most affected brain regions. The disease-specific atlases were created independently for multiple MR contrasts (e.g., $T_1$-weighted image, $T_2$ map, and DTI) using a training dataset. Assuming that there are multiple pathologies with different spatial distribution in a single disease (e.g., neuronal loss, demyelination, ischemic changes, etc.), it may be further hypothesized that the optimized combination of multiple MR contrasts could increase the power to separate diseased brains from normal brains. Therefore, the MR measures of each contrast from the corresponding disease-specific atlas were optimally combined using the linear discriminant analysis.

It should be noted that any software associated with the present invention is programmed onto a non-transitory computer readable medium that can be read and executed by any of the computing devices mentioned in this application, such as smart watches, smart wearables, smart phones, tablets, phablets, laptop computers, personal computers, servers etc. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, or any other suitable data transmission means known to or conceivable by one of skill in the art.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A non-invasive imaging system, comprising:
   an imaging scanner configured to generate an imaging signal from a tissue region of a subject under observation, the tissue region having at least one substructure wherein the imaging signal comprises image data;
   a non-transitory computer readable medium programmed for:
   receiving the imaging signal from the imaging scanner;
   accessing an anatomical atlas comprising geometric information corresponding to said at least one substructure in the tissue region, and accessing a pathological atlas corresponding to an abnormality of said tissue region, wherein the pathological atlas comprises first statistical information regarding voxels of the abnormality after being registered to at least a portion of the geometric information in the anatomical atlas;
   transforming the imaging signal to register the tissue region to at least a portion of the geometric information in the anatomical atlas, wherein a registered tissue region image is obtained;
   determining second statistical information regarding voxels of the registered tissue region image corresponding to said at least one substructure;
   identifying automatically, based on the first statistical information and the second statistical information, a presence of said abnormality or a pre-cursor abnormality thereof in said tissue region of said subject under observation;
   updating the image data with data from the pathological atlas; and
   displaying the updated image data.

2. The non-invasive imaging system according to claim 1, wherein said imaging scanner is a magnetic resonance imaging (MRI) scanner, a computed tomography (CT) imaging scanner, a positron emission tomography (PET) imaging scanner, a single positron emission computed tomography (SPECT) imaging scanner, or a combination thereof.

3. The non-invasive imaging system according to claim 1 further comprising the nontransitory computer readable medium being programmed for superimposing the pathological atlas and the anatomical atlas on the image data.

4. The non-invasive imaging system according to claim 1, wherein said imaging scanner is capable of providing at least one contrast mechanism that delineates at least a portion of said at least one substructure of said tissue region.

5. The non-invasive imaging system according to claim 4, wherein the non-transitory computer readable medium is further programmed for identifying automatically the presence of said abnormality by utilizing said at least one contrast mechanism.

* * * * *